(12) United States Patent
Kinkade et al.

(10) Patent No.: US 10,335,265 B2
(45) Date of Patent: Jul. 2, 2019

(54) RING ON A CLOSED WEB STENT-GRAFT FOR USE IN TIP CAPTURE

(71) Applicant: Medtronic Vascular, Inc., Santa Rosa, CA (US)

(72) Inventors: Jeremy Kinkade, Santa Rosa, CA (US); Mark Stiger, Windsor, CA (US); Brandon Woll, Santa Rosa, CA (US); Joshua Schmitt, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 665 days.

(21) Appl. No.: 14/509,128

(22) Filed: Oct. 8, 2014

(65) Prior Publication Data

US 2015/0025617 A1    Jan. 22, 2015

Related U.S. Application Data

(63) Continuation of application No. 13/457,888, filed on Apr. 27, 2012, now Pat. No. 8,882,828.

(51) Int. Cl.
*A61F 2/07* (2013.01)
*A61F 2/95* (2013.01)
*A61F 2/966* (2013.01)

(52) U.S. Cl.
CPC .............. *A61F 2/07* (2013.01); *A61F 2/95* (2013.01); *A61F 2/966* (2013.01); *A61F 2002/075* (2013.01); *A61F 2002/9511* (2013.01)

(58) Field of Classification Search
CPC .... A61F 2/07; A61F 2/95; A61F 2/954; A61F 2002/072; A61F 2002/075; A61F 2002/077; A61F 2002/9505; A61F 2002/9511; A61F 2002/9528; A61F 2002/9534

See application file for complete search history.

(56) References Cited

U.S. PATENT DOCUMENTS

| | | | |
|---|---|---|---|
| 5,507,771 A * | 4/1996 | Gianturco | A61F 2/07 606/191 |
| 6,352,553 B1 | 3/2002 | Van der Burg et al. | |
| 6,361,545 B1 | 3/2002 | Macoviak et al. | |
| 6,565,597 B1 * | 5/2003 | Fearnot | A61F 2/07 623/1.13 |
| 6,645,239 B1 | 11/2003 | Park et al. | |
| 7,815,591 B2 * | 10/2010 | Levine | A61F 2/04 604/8 |
| 7,819,836 B2 * | 10/2010 | Levine | A61F 5/0076 604/8 |
| 8,043,357 B2 | 10/2011 | Hartley | |

(Continued)

*Primary Examiner* — Dianne Dornbusch

(57) ABSTRACT

A stent-graft has a closed web end configuration in which endmost stent crowns do not extend beyond an end or edge of a tubular graft. In order to couple the stent-graft to tip capture fingers or prongs of a delivery system, the stent-graft includes a ring woven between the endmost crowns of an end stent. When end stent is in a compressed delivery configuration, sections of the ring between adjacent endmost crowns form attachment loops that longitudinally extend beyond the end of the tubular graft for engaging the tip capture fingers of a delivery system. When the end stent is in an expanded fully deployed configuration, the attachment loops retract back to the stent so that the ring is a circular band having a diameter substantially equal to the expanded diameter of the stent.

20 Claims, 10 Drawing Sheets

(56) References Cited

U.S. PATENT DOCUMENTS

| | | | |
|---|---|---|---|
| 8,062,345 B2 | 11/2011 | Ouellette et al. | |
| 8,449,595 B2 | 5/2013 | Quellette et al. | |
| 8,771,219 B2* | 7/2014 | Meade | 604/8 |
| 9,314,356 B2* | 4/2016 | McHugo | A61F 2/966 |
| 9,427,317 B2* | 8/2016 | Styrc | A61F 2/2439 |
| 2002/0120277 A1* | 8/2002 | Hauschild | A61B 17/221 |
| | | | 606/108 |
| 2002/0188344 A1* | 12/2002 | Bolea | A61F 2/90 |
| | | | 623/1.11 |
| 2003/0120332 A1 | 6/2003 | Hartley | |
| 2005/0038455 A1* | 2/2005 | Bates | A61F 2/064 |
| | | | 606/153 |
| 2005/0049674 A1* | 3/2005 | Berra | A61F 2/07 |
| | | | 623/1.13 |
| 2005/0288768 A1* | 12/2005 | Sowinski | A61F 2/07 |
| | | | 623/1.13 |
| 2006/0142836 A1* | 6/2006 | Hartley | A61F 2/07 |
| | | | 623/1.11 |
| 2006/0190075 A1* | 8/2006 | Jordan | A61F 2/90 |
| | | | 623/1.23 |
| 2006/0276887 A1* | 12/2006 | Brady | A61F 2/90 |
| | | | 623/1.53 |
| 2007/0135889 A1* | 6/2007 | Moore | A61F 2/07 |
| | | | 623/1.13 |
| 2008/0046065 A1 | 2/2008 | Hartley et al. | |
| 2008/0140178 A1* | 6/2008 | Rasmussen | A61F 2/95 |
| | | | 623/1.11 |
| 2008/0234834 A1* | 9/2008 | Meade | A61B 17/221 |
| | | | 623/23.65 |
| 2008/0243225 A1* | 10/2008 | Satasiya | A61F 2/91 |
| | | | 623/1.12 |
| 2008/0264102 A1 | 10/2008 | Berra | |
| 2009/0099640 A1* | 4/2009 | Weng | A61F 2/95 |
| | | | 623/1.11 |
| 2009/0192585 A1* | 7/2009 | Bloom | A61F 2/2412 |
| | | | 623/1.11 |
| 2009/0216308 A1* | 8/2009 | Hartley | A61F 2/07 |
| | | | 623/1.11 |
| 2009/0270971 A1* | 10/2009 | Xiao | A61F 2/07 |
| | | | 623/1.14 |
| 2009/0276027 A1 | 11/2009 | Glynn | |
| 2010/0016944 A1* | 1/2010 | Styrc | A61F 2/95 |
| | | | 623/1.11 |
| 2010/0168838 A1* | 7/2010 | Hartley | A61F 2/95 |
| | | | 623/1.11 |
| 2011/0071613 A1* | 3/2011 | Wood | A61F 2/88 |
| | | | 623/1.11 |
| 2011/0118816 A1 | 5/2011 | Jensen et al. | |
| 2012/0041538 A1* | 2/2012 | White | A61F 2/885 |
| | | | 623/1.12 |
| 2012/0136425 A1* | 5/2012 | Orr | A61F 2/95 |
| | | | 623/1.11 |
| 2012/0310327 A1* | 12/2012 | McHugo | A61F 2/90 |
| | | | 623/1.15 |

* cited by examiner

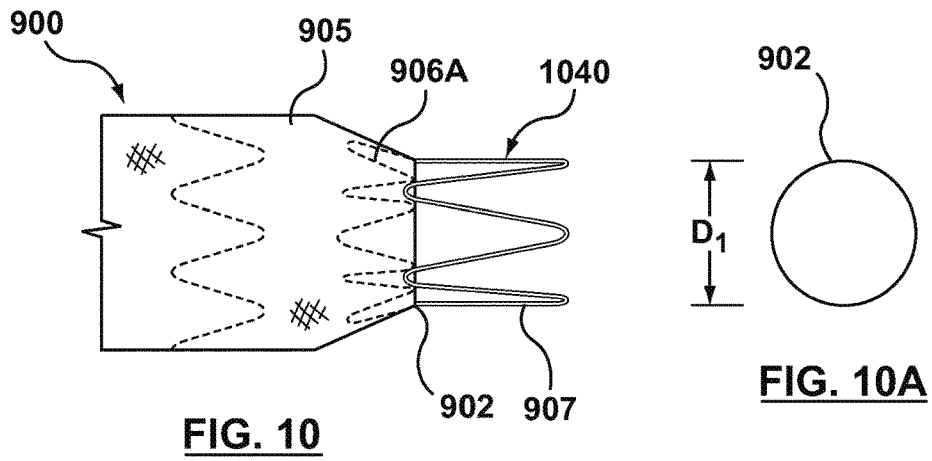
FIG. 10
FIG. 10A
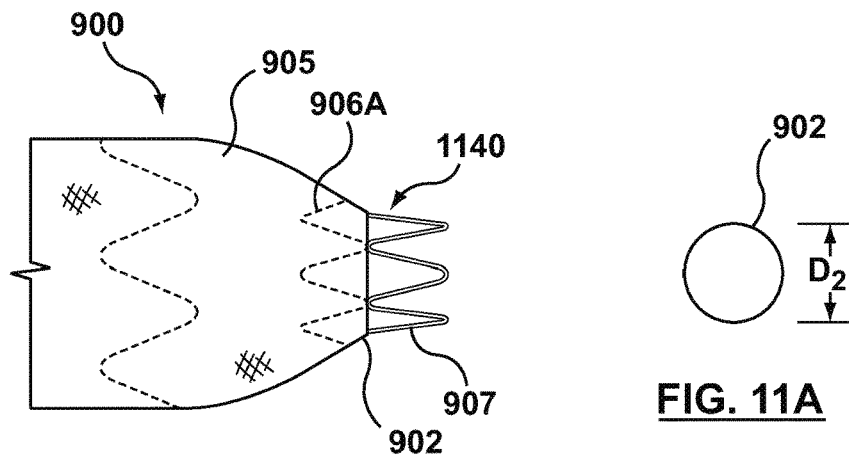
FIG. 11
FIG. 11A
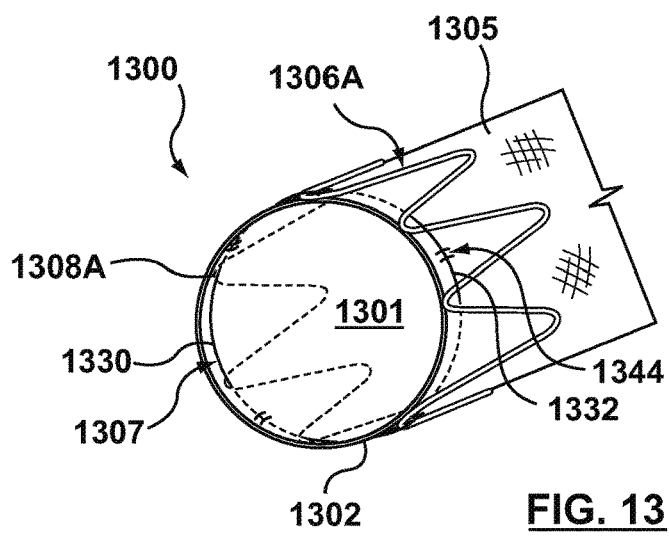
FIG. 13

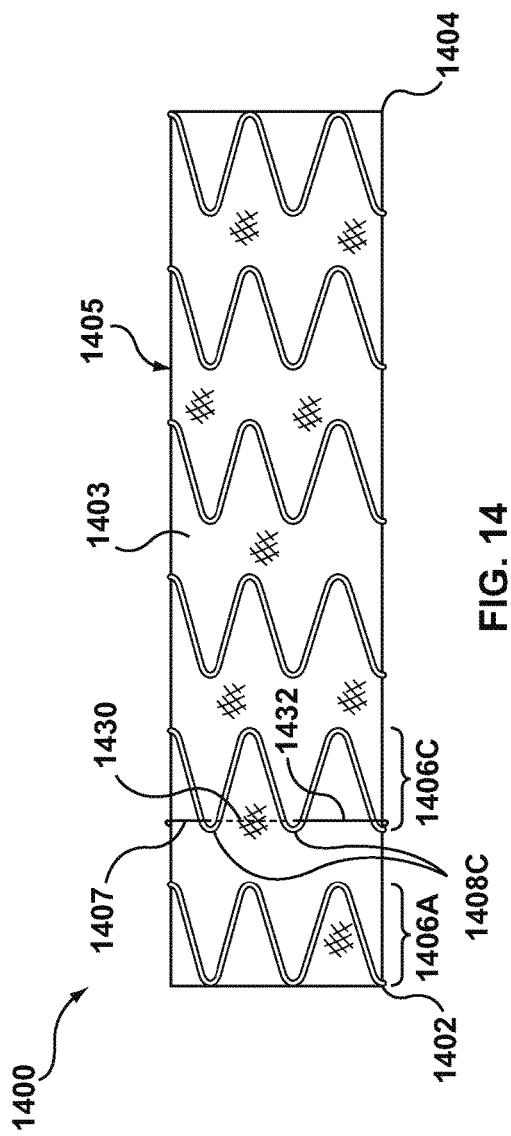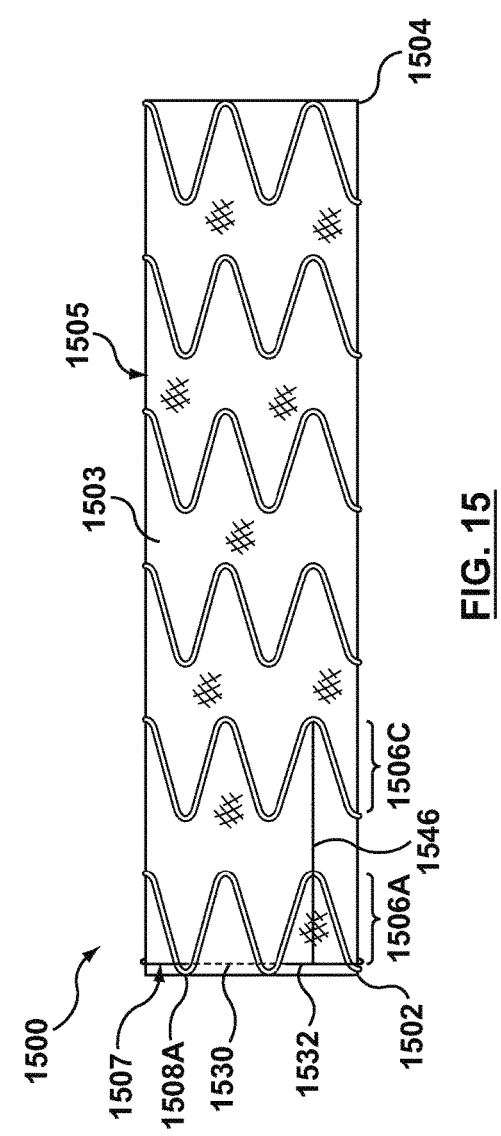

RING ON A CLOSED WEB STENT-GRAFT FOR USE IN TIP CAPTURE

CROSS-REFERENCE TO RELATED APPLICATIONS

This application claims the benefit of U.S. patent application Ser. No. 13/457,888, filed Apr. 27, 2012, which is hereby incorporated by reference in its entirety for all purposes.

FIELD OF THE INVENTION

The invention is related in general to implantable prostheses and in particular to self-expanding stent-grafts.

BACKGROUND OF THE INVENTION

Prostheses for implantation in blood vessels or other similar organs of the living body are, in general, well known in the medical art. For example, prosthetic endovascular grafts constructed of biocompatible materials have been employed to replace or bypass damaged or occluded natural blood vessels. In general, endovascular grafts include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expanded stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes or shafts arranged for relative axial movement. For example, a self-expanding stent-graft may be compressed and disposed within a distal end of an outer shaft or sheath component of the delivery catheter distal of a stop fixed to an inner shaft or member. The delivery catheter is then maneuvered, typically tracked through a body lumen until a distal end of the delivery catheter and the stent-graft are positioned at the intended treatment site. The stop on the inner member is then held stationary while the sheath component of the delivery catheter is withdrawn. The stop on the inner member prevents the stent-graft from being withdrawn with the sheath component. As the sheath component is withdrawn, the stent-graft is released from the confines thereof and radially self-expands so that at least a portion of it contacts and substantially conforms to a portion of the surrounding interior of the lumen, e.g., the blood vessel wall or anatomical conduit.

In recent years, to improve optimal control and alignment during deployment and positioning of a stent-graft, various tip capture mechanisms have been incorporated into the delivery system utilized for percutaneously delivering the prosthesis. Tip capture involves restraining a proximal end stent of the stent-graft in conjunction with a main body restraint achieved by other delivery system components, such as a tubular outer shaft or sheath component. The tip capture mechanism can be activated at any time during stent-graft deployment to suit any number of system characteristics driven by the therapy type, stent-graft type, or specific anatomical conditions that may prescribe the release timing. Typically, the tip capture release is activated after some or all of the main stent-graft body release, and thus provides a means of restraining the stent-graft during positioning. Additional restraint of the stent-graft is a key characteristic when the operator is attempting to accurately position the stent relative to an anatomical target.

For example, U.S. Patent Application Publication No. 2006/0276872 to Arbefuielle et al. and U.S. Patent Application Publication No. 2009/0276207 to Glynn et al., both herein incorporated by reference in their entirety, describe tip capture mechanisms that restrain a proximal end stent of the stent-graft while the remainder of the stent-graft expands, then releases the proximal end stent. The proximal end stent is attached to the graft material of the stent-graft so as to have an "open web" or "free flow" proximal end configuration in which the endmost crowns thereof extend past or beyond the graft material such that the endmost crowns are exposed or bare, and thus free to interact with a tip capture mechanism and couple the prosthesis to the delivery system. The open web proximal end configuration allows blood flow through the endmost crowns for perfusion during and/or after implantation. FIGS. 1A and 1B illustrate a delivery system 10 having a tip capture mechanism 12 designed to couple or interact with a stent-graft 14 having an open web or free flow proximal end configuration 16. More particularly, endmost crowns 18 of a proximal end stent 15 engage or extend around retractable finger or prong-like elements 20 of the tip capture mechanism. When an outer delivery shaft 22 is retracted to allow stent-graft 14 to self-expand, endmost crowns 18 of the proximal end stent 15 remain engaged around tip capture fingers 20, as shown in FIG. 1A. To release proximal end stent 15, a shaft 24 coupled to finger or prong-like elements 20 is refracted and end stent 15 is allowed to self-expand, as shown in FIG. 1B. The Captiva Delivery System manufactured by Medtronic Vascular, Inc. of Santa Rosa, Calif. is one example of a delivery system having a tip capture mechanism as described above, which may be utilized for delivering endovascular stent-grafts such as the Valiant Thoracic Stent-graft manufactured by Medtronic Vascular, Inc. of Santa Rosa, Calif.

Tip capture mechanisms have improved accuracy of deployment of self-expanding stent-grafts having open web or free flow configurations. However, in some cases a closed web configuration may be required or chosen due to application and/or user preferences. In a closed web configuration, the endmost crowns do not extend past or beyond the graft material but rather are covered or lined by graft material. For example, a stent-graft having a closed web configuration may be selected to treat dissections or vessel transections due to the related condition of the vessel tissue. In these cases, the tissue is fragile and may be damaged by exposed stent struts or apices. A closed web stent-graft thus presents a proximal configuration that is less traumatic to sensitive tissues or disease states. However, stent-grafts having a closed web proximal configuration do not have a bare proximal end stent free to interact with a tip capture mechanism of a delivery system, and thus may present challenges during deployment with varied success of achieving control during delivery without utilizing tip capture. Embodiments hereof relate to a stent-graft having a closed web proximal end configuration that may interact with a tip capture mechanism of a delivery system.

BRIEF SUMMARY OF THE INVENTION

Embodiments hereof relate to a prosthesis for implantation within a body lumen, the prosthesis including a tubular graft of a graft material and a stent coupled to the tubular graft. The stent includes a plurality of crowns and a plurality of struts with each crown being formed between a pair of opposing struts. The stent has endmost crowns that are adjacent to and distal of a proximal edge of the tubular graft. The endmost crowns are covered by the graft material of the tubular graft. A ring engages each of the endmost crowns of the stent with sections of the ring being defined between adjacent endmost crowns. At least one of the sections of the ring longitudinally extends beyond the proximal edge of the tubular graft as an attachment loop of the prosthesis when the stent is in a compressed delivery configuration. When the stent is in an expanded deployed configuration, the ring is a circular band.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 5-8 illustrate a method of deploying the stent-graft prosthesis of FIG. 2, wherein FIGS. 5-6 illustrate the stent-graft prosthesis in a delivery configuration, FIG. 7 illustrates the stent-graft prosthesis in a partially deployed configuration, and FIG. 8 illustrates the stent-graft prosthesis in a fully deployed configuration.

FIG. 10 is a side view of a portion of the stent-graft prosthesis of FIG. 9, wherein the stent-graft prosthesis is in a partially deployed configuration and every other section of the ring forms a temporary attachment loop for coupling to a delivery system.

FIG. 10A is an end view of FIG. 10.

FIG. 11 is a side view of a portion of the stent-graft prosthesis of FIG. 9, wherein the stent-graft prosthesis is in a partially deployed configuration and every section of the ring forms a temporary attachment loop for coupling to a delivery system.

FIG. 11A is an end view of FIG. 11.

FIG. 13 is a perspective end view of a stent-graft prosthesis having a ring that is woven between adjacent endmost crowns of an end stent of the stent-graft, wherein interior and exterior sections of the ring extend between adjacent endmost crowns and alternate between inside and outside surfaces of the graft of the stent-graft, with stitches coupling the exterior sections of the ring to the graft according to an embodiment hereof.

FIG. 14 is a side view of a stent-graft prosthesis having a ring that is woven between adjacent endmost crowns of a stent adjacent to an end stent of the stent-graft according to another embodiment hereof.

FIG. 15 is a side view of a stent-graft prosthesis having a ring that is woven between adjacent endmost crowns of an end stent of the stent-graft, wherein a suture extends from the ring to a stent adjacent to the end stent of the stent-graft according to another embodiment hereof.

DETAILED DESCRIPTION OF EMBODIMENTS OF THE INVENTION

Figure 1A:
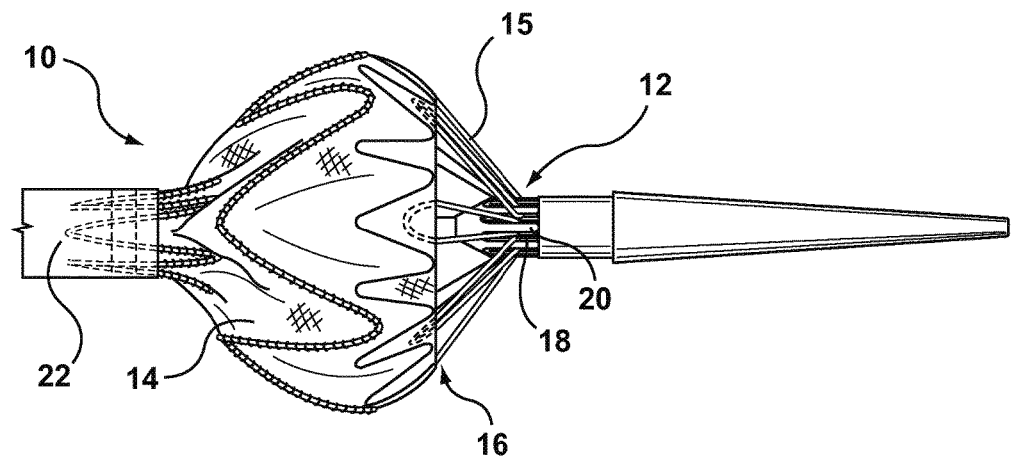
FIGS. 1A and 1B are side views of a distal end of a delivery system having a tip capture mechanism designed to couple or interact with a stent-graft having an open web or free flow proximal end configuration.
Figure 1B:
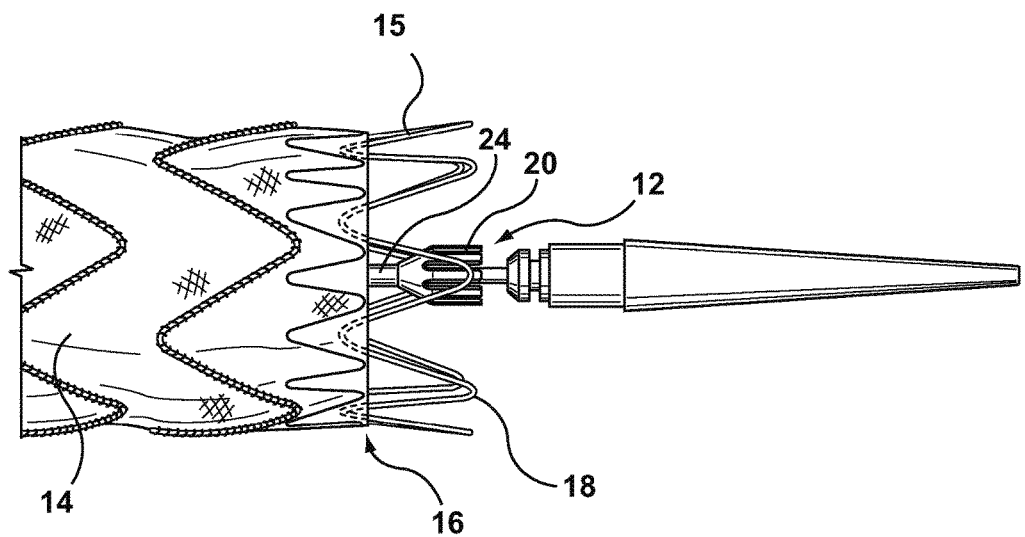

Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft prosthesis "proximal" is the portion nearer the heart by way of blood flow path while "distal" is the portion of the stent-graft further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments hereof relate to a stent-graft prosthesis having a closed web end configuration, and more particularly relate to an apparatus and method for securing a stent-graft prosthesis having a closed web end configuration to tip capture fingers or prongs of a delivery system. As will be explained in more detail below, the stent-graft prosthesis includes a strand of material that is woven between adjacent endmost crowns of the stent-graft to form a ring with sections of the ring being defined between adjacent endmost crowns. One or more section(s) of the ring transform or transition into attachment loops for coupling or hitching to tip capture fingers or prongs of a delivery system. Additional description and features are described below with reference to the figures.

Figure 2:
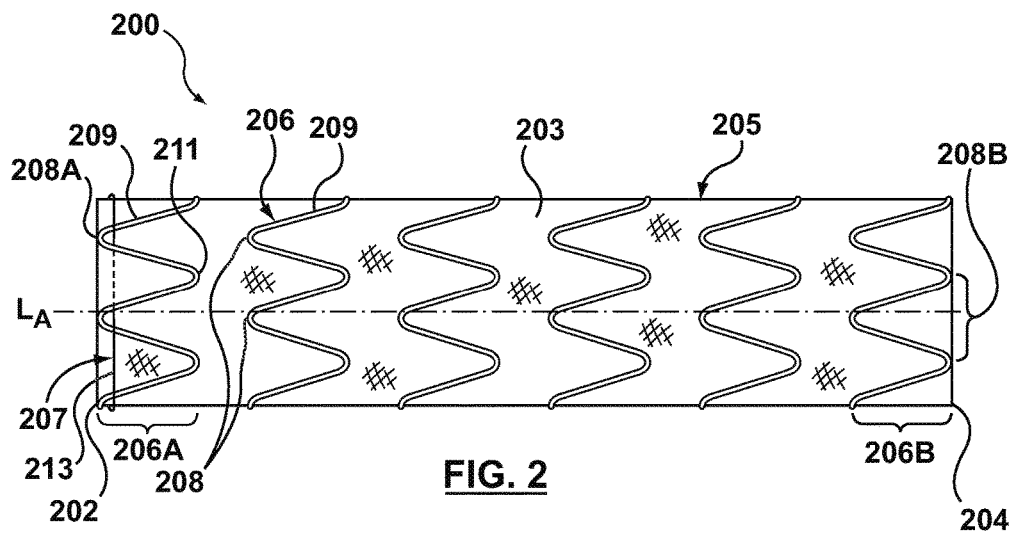
FIG. 2 is a side view of a stent-graft prosthesis having a ring that is woven between adjacent endmost crowns of an end stent of the stent-graft, wherein interior and exterior sections of the ring extend between adjacent endmost crowns and alternate between inside and outside surfaces of the graft of the stent-graft according to an embodiment hereof.
Figure 3:
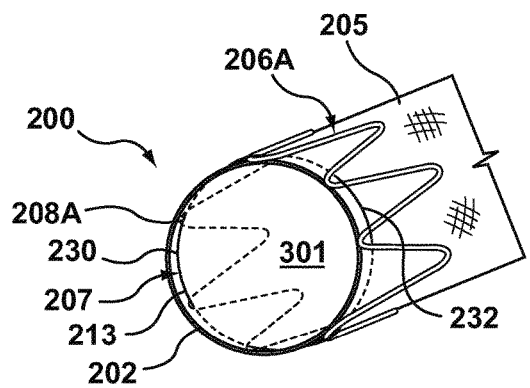
FIG. 3 is a perspective end view of a portion of the stent-graft prosthesis of FIG. 2.

Referring to FIG. 2-3, stent-graft prosthesis 200 includes a tubular graft 205 having a longitudinal axis $L_A$, first edge or end 202, a second edge or end 204, and a body 203 there between which defines a lumen 301 through stent-graft prosthesis 200. In an embodiment, first edge 202 of tubular graft 205 may be referred to as a proximal end or edge of tubular graft 205 and a proximal end or edge of stent-graft prosthesis 200, which is conventionally the end that is coupled to a tip capture mechanism of a delivery system, and second edge 204 of tubular graft 205 may be referred to as a distal end or edge of graft 204 and a distal end or edge of stent-graft prosthesis 200. Tubular graft 205 may be formed from any suitable graft material, for example and not limited to, a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa.

Stent-graft prosthesis 200 also includes at least one radially-compressible stent or scaffold 206 that is coupled to tubular graft 205 for supporting the graft material and is operable to self-expand into apposition with an interior wall of a body vessel (not shown). In the embodiment depicted in FIG. 2, stent-graft prosthesis 200 is shown in its fully expanded or deployed configuration and includes a series of six independent or separate cylindrical stents 206. Each stent 206 is constructed from a self-expanding or spring material, such as Nitinol, and is a sinusoidal patterned ring including a plurality of crowns or bends 208 and a plurality of struts or straight segments 209 with each crown being formed between a pair of opposing struts. Although shown with six stents, it will be understood by one of ordinary skill in the art that stent-graft prosthesis 200 may include a greater or smaller number of stents depending upon the desired length of stent-graft prosthesis 200 and/or the intended application thereof. For description purposes only, the stent that is coupled adjacent and proximate to first edge 202 of tubular graft 205 is referred to herein as first or proximal end stent 206A and the stent that is coupled adjacent and proximate to second edge 204 of tubular graft 205 is referred to herein as second or distal end stent 206B. Proximal end stent 206A is coupled to tubular graft 205 distal to first or proximal edge 202 of tubular graft 205. Stents 206 are shown in FIG. 2 has having identical sinusoidal patterns but it will be understood by one of ordinary skill in the art that one or more of stents 206 may have a different pattern or configuration. Stents 206 are coupled to tubular graft 205 by stitches or other means known to those of skill in the art. In the embodiment shown in FIG. 2, stents 206 are coupled to an outside surface of tubular graft 205. However, stents 206 may alternatively be coupled to an inside surface of tubular graft 205. When stent-graft prosthesis 200 is used for treating an aneurysm, stents 206 have sufficient radial spring force and flexibility to conformingly engage stent-graft prosthesis 200 with the body lumen inner wall, to avoid excessive leakage, and prevent pressurization of the aneurysm, i.e., to provide a leak-resistant seal. Although some leakage of blood or other body fluid may occur into the aneurysm isolated by stent-graft prosthesis 200, an optimal seal will reduce the chances of aneurysm pressurization and resulting rupture.

At least first edge 202 of stent-graft prosthesis 200 has a closed web configuration in which endmost crowns 208A of first end stent 206A are covered or lined by tubular graft 205 and do not extend past or beyond first edge 202 of tubular graft 205. As utilized herein, "endmost" crowns are the crowns or peaks of a stent that are most proximate to and inwardly spaced apart from an end or edge of tubular graft 205, such as first edge 202. In the embodiment of FIG. 2, end stent 206A is coupled to the graft material so as to have a first set of endmost crowns 208A adjacent to and distal of first or proximal edge 202 of tubular graft 205 and a second or opposing set of crowns 211 distant from first or proximal edge 202 of tubular graft 205 relative to the first set of endmost crowns. Endmost crowns 208A of end stent 206A may be stitched or otherwise secured to tubular graft 205. In the embodiment depicted in FIG. 2, endmost crowns 208B of distal end stent 206B are also covered or lined by tubular graft 205, i.e, do not extend outside of or beyond second edge 204 of tubular graft 205, and are stitched or otherwise secured to tubular graft 205. In another embodiment hereof (not shown), endmost crowns 208B of second edge stent 206B may extend beyond second edge 204 of tubular graft 205 in an open web or free-flow configuration.

Rather than utilizing endmost crowns 208A of first end stent 206A to couple the prosthesis to a delivery system as in open-web or free-flow configurations, prosthesis 200 includes a ring 207 to couple the prosthesis to a delivery system during initial deployment. Ring 207 is a strand 213 of material that forms a continuous hoop or circular band having a diameter substantially equal to the expanded diameter of end stent 206A. As utilized herein, "substantially equal to" the expanded diameter of an end stent includes a ring or circular band having a diameter equal to the expanded diameter of the end stent with a 5% margin of error. In an embodiment, the expanded outer diameter of end stent 206A, as well as the diameter of ring 207, may be intentionally oversized with respect to the target vessel and be between 5% and 20% greater than the diameter of the target inner vessel wall. For example, stent-graft prosthesis 200 may have a 40 mm expanded diameter for a target vessel ranging from 38 mm, in the case of a dissection or transection, to 32 mm, in the case of an aneurysm. Thus, when implanted within the target vessel and thus restricted to the smaller lumenal diameter thereof, an over-sized ring 207 may not extend to its full diameter and excess material of ring 207 may reside on the inside or outside of the stent-graft.

Figure 4:
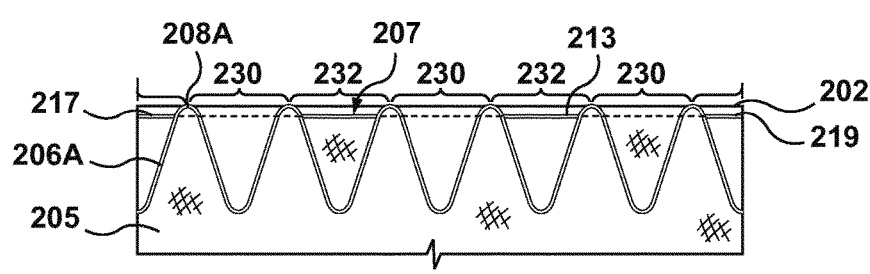
FIG. 4 is a side view of the end of the stent-graft prosthesis of FIG. 2, wherein the stent-graft prosthesis has been cut and laid out flat for illustrative purposes only.

Ring 207 engages or extends through each endmost crown 208A of end stent 206A. As best shown in FIGS. 3 and 4, a first end 217 of strand 213 pierces and is threaded through the graft material of tubular graft 205 within each endmost crowns 208A of first end stent 206A until the strand is woven between adjacent endmost crowns 208A of first end stent 106A and extends around the circumference of end stent 206A. Once strand 213 extends around the circumference of end stent 206A, first end 217 of strand 213 is then coupled or attached to a second end 219 of strand 213 to form ring 207. Each endmost crown 208A of end stent 206A is ensnared or captured by ring 207. Ring 207 includes a plurality of integral sections which each extend between adjacent endmost crowns 208A and collectively encircle endmost crowns 208A of stent 206A as a circular band. In the embodiment of FIG. 2, sections of ring 207 extending between adjacent endmost crowns 208A alternate between inside and outside surfaces of tubular graft 205. More particularly, interior sections or portions 230 of ring 207 extends between adjacent endmost crowns 208A along an inside surface of tubular graft 205, and exterior sections or portions 232 of ring 207 extend between adjacent endmost crowns 208A along an outside surface of tubular graft 205. Besides being woven between endmost crowns 208A of first end stent 206A, ring 207 is not stitched or otherwise attached to prosthesis 200 and is therefore allowed to slide through or freely rotate between the stent crowns.

Figure 5:
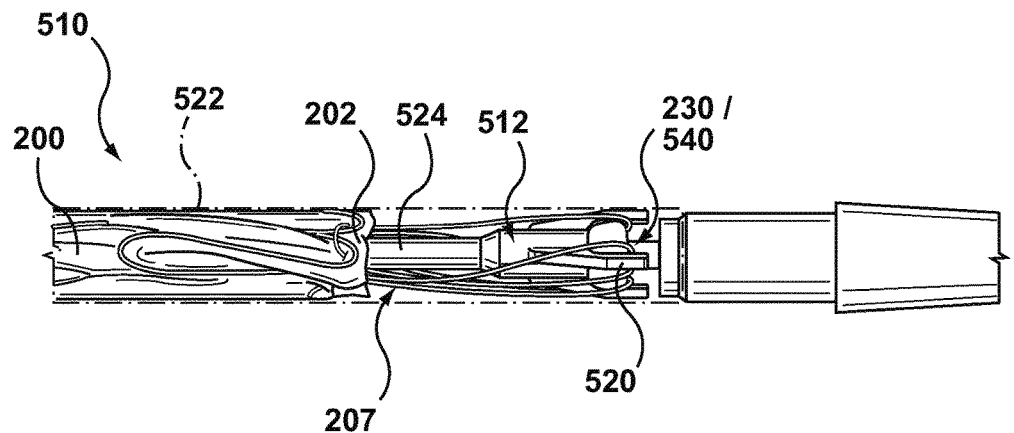
Figure 6:
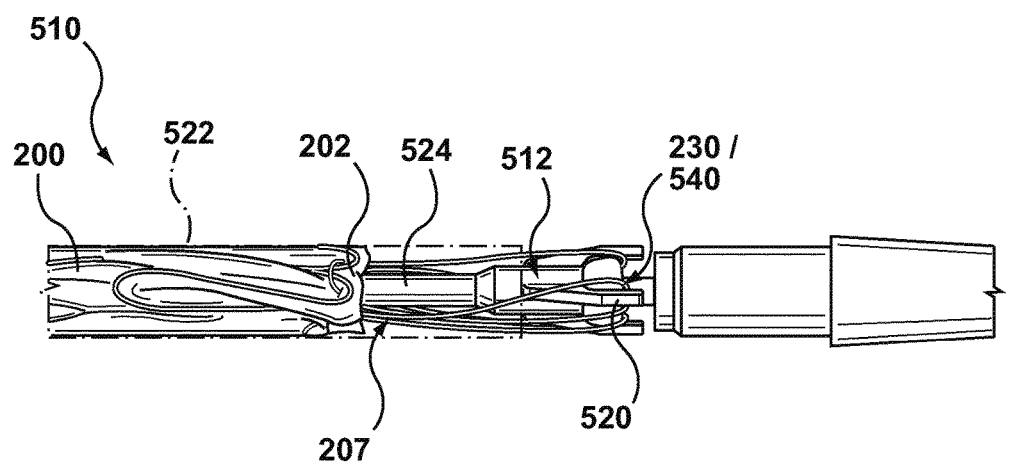

Referring now to FIGS. 5-8, ring 207 is utilized for coupling first edge 202 of prosthesis 200 to a retractable tip capture spindle 512 of a delivery system 510. Delivery system 510 includes at least an outer delivery sheath 522 and a catheter shaft 524 having tip capture spindle 512 mounted thereon. Prosthesis 200 is also mounted on catheter shaft 524 and outer delivery sheath 522 covers and restrains prosthesis 200 in a compressed configuration for delivery thereof. In an embodiment, delivery system 510 is the Captiva Delivery System, manufactured by Medtronic Vascular, Inc. of Santa Rosa, Calif., or is a delivery system as described in U.S. Patent Application Publication No. 2009/0276207 to Glynn et al., previously incorporated by reference in its entirety. Only a distal end of delivery system 510 is shown in the figures. FIGS. 5 and 6 illustrate prosthesis 200 in a delivery configuration, in which prosthesis 200 is mounted on catheter shaft 524 with outer delivery sheath 522 covering and restraining prosthesis 200 in a compressed configuration for delivery thereof. Interior sections 230 of ring 207 transform or transition into temporary attachment loops 540 that longitudinally extend, i.e., extend in the direction of longitudinal axis $L_A$ of tubular graft 205 shown in FIG. 2, beyond first or proximal edge 202 of prosthesis 200 and engage or extend around prong or finger-like elements 520 of tip capture spindle 512. In another embodiment (not shown), exterior sections 232 of ring 207 may alternatively transform or transition into temporary attachment loops 540. FIG. 6 illustrates prosthesis 200 in a delivery configuration with outer delivery sheath 522 slightly trimmed or cut back to expose tip capture fingers 520 for illustrative purposes.

Figure 7:
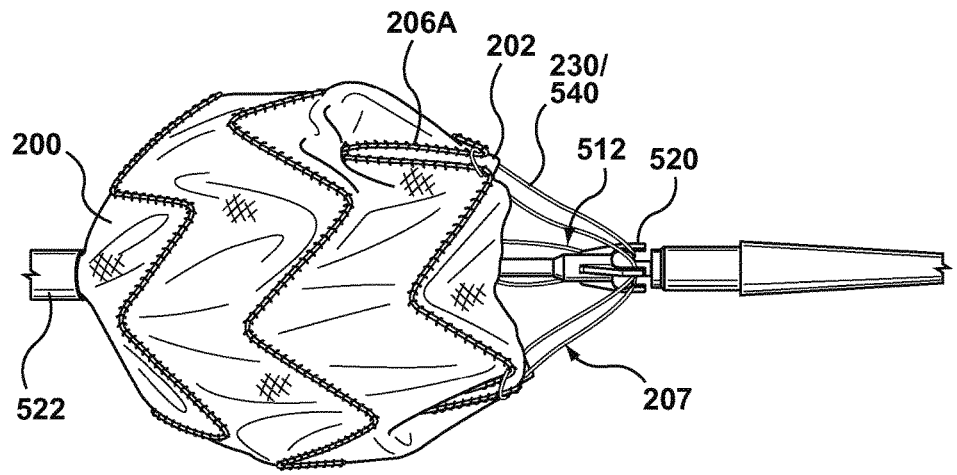

When initial or partial deployment of prosthesis 200 is desired, outer delivery sheath 522 is retracted to allow body 203 of prosthesis 200 to self-expand. As shown in FIG. 7, when stent-graft prosthesis 200 is in a partially deployed configuration, interior sections 230 of ring 207 remain engaged with tip capture fingers 520 and first end stent 206A is allowed to partially open or deploy, thereby allowing blood flow through stent-graft prosthesis 200. Notably, prosthesis 200 is still coupled to delivery system 510 via ring 207 to permit repositioning if required.

Figure 8:
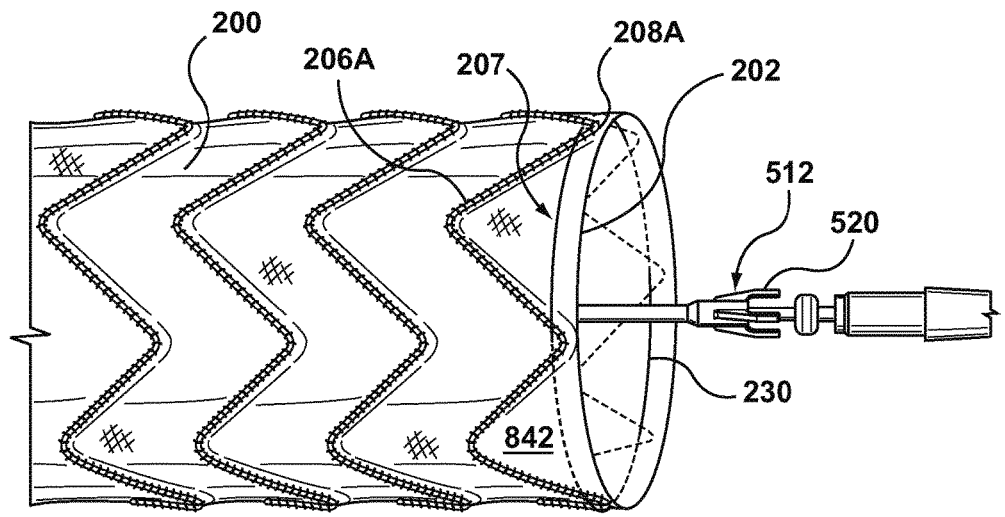

After any and all repositioning is performed and prosthesis 200 is positioned as desired, prosthesis 200 may be finally deployed and released from delivery system 510 by retracting catheter shaft 524 and thereby retracting tip capture spindle 512. Tip capture fingers 520 are retracted and are disengaged from interior sections 230 of ring 207. When ring 207 is no longer coupled to delivery system 510, first end stent 206A is permitted to fully expand or deploy as shown in FIG. 8. As first end stent 206A expands, temporary attachment loops 540 are pulled back or retract towards stent 206A such that interior sections 230 of ring 207 resume extending along an inside surface of graft 205 as described with respect to FIGS. 2-4, and ring 207 is a circular band that encircles endmost crowns 208A of end stent 206A. When first end stent 206A reaches its fully deployed expanded diameter, ring 207 is completely pulled back into end stent 206A and no sections of ring 207 extend beyond the first or proximal edge 202 of tubular graft 205. The fully deployed or expanded configuration of prosthesis 200 is thus a closed web configuration in which neither endmost crowns 208A of first end stent 206A nor ring 207 extend past first or proximal edge 202 of prosthesis 200. When deployed in situ, ring 207 has substantially the same diameter as expanded end stent 206A and is therefore taut or tightly stretched between endmost crowns 208A of end stent 206A. In an embodiment, interior sections 230 of ring 207 restrain or hold open flaps 842 of graft material extending between endmost crowns 208A of first end stent 206A. The tautness of ring 207 between endmost crowns 208A of end stent 206A allows interior sections 230 to impart enough force on flaps 842 to keep the flaps open and pressed against the vessel wall.

In coupling prosthesis 200 to delivery system 510, ring 207 provides the advantages of a free-flow or open web proximal end configuration to prosthesis 200 during initial or partial deployment while retaining the closed web configuration of prosthesis 200 after full or final deployment. More particularly, as described above with respect to FIG. 7, the partially deployed configuration of first end stent 206A allows blood flow there through while prosthesis 200 is still coupled to delivery system 510 via ring 207 for repositioning if required. Since blood flow is allowed through partially deployed prosthesis 200, ring 207 reduces the issue of blood flow impacting the outer surface of prosthesis 200 during initial or partial deployment, otherwise known as the "watermelon seed" effect in which blood flow against an outer surface of the prosthesis may unintentionally force the prosthesis downstream during final deployment thereof. If closed-web endmost crowns of an end stent were coupled to a tip capture mechanism without ring 207, the graft extends all the way to the delivery system and provides an increased surface area that the blood flows acts on, thereby increasing the watermelon seed effect. However, ring 207 prevents such increased surface area because it allows blood to flow through attachment loops 540 of the partially deployed prosthesis 200 similar to prostheses having open-web or free-flow proximal end configurations. However, unlike prostheses having free-flow or open web proximal end configurations, attachment loops 540 formed by ring 207 retract back within tubular graft 205 after release from the delivery system so that prosthesis 200 has a closed-web proximal end configuration after final deployment.

In addition, ring 207 allows a greater length or amount of body 203 of prosthesis 200 to expand into apposition with the vessel wall during initial or partial deployment as compared to a configuration which uses an end stent of a stent-graft to couple the stent-graft to a delivery system. More particularly, as described above with respect to FIG. 7, when partially deployed the interior sections 230 of ring 207 transition into attachment loops 540 that extend beyond first edge 202 of prosthesis 200 and engage or extend around prong or finger-like elements 520 of tip capture spindle 512. As such, attachment loops 540 separate or distance tubular graft 205 from delivery system 510. As compared to stent-grafts having open-web or free-flow proximal end configurations that engage the delivery system, attachment loops 540 increase the distance between first end stent 206A and the delivery system tip capture spindle 512 and a greater length of prosthesis is allowed to deploy or expand into apposition with the vessel wall while ring 207 is still coupled to delivery system 510, i.e., pre-tip release. The increased amount of apposition helps to prevent the watermelon seed effect.

As compared to stents 206, ring 207 is not expanding or opening prosthesis 200 and thus is not required to be formed of a spring material having sufficient force to deploy prosthesis 200. Ring 207 may be formed from Nitinol (NiTi), a nickel-titanium alloy, or various suture compositions. If formed from Nitinol (NiTi) or another material that may be shape set, ring 207 may be shape set as a circular band that has a diameter substantially equal to the diameter of expanded stent 206A. Shape setting ring 207 is not required, but helps to ensure that attachment loops 540 of ring 207 completely recoil or retract into tubular graft 205 upon full deployment of prosthesis 200.

Figure 9:
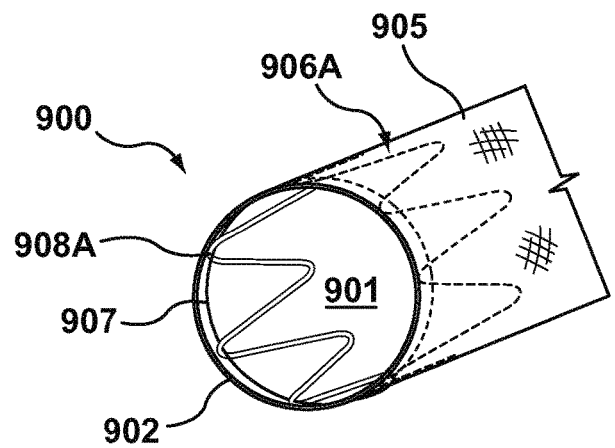
FIG. 9 is a perspective end view of a portion of a stent-graft prosthesis having a ring that is woven between adjacent endmost crowns of an end stent of the stent-graft, wherein sections of the ring that extend between adjacent endmost crowns extend along the inside surface of the graft of the stent-graft according to another embodiment hereof.
Figure 9A:
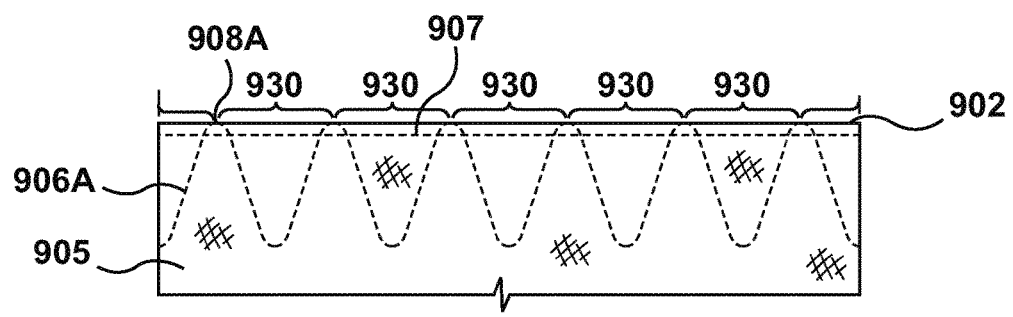
FIG. 9A is a side view of the end of the stent-graft prosthesis of FIG. 9, wherein the stent-graft prosthesis has been cut and laid out flat for illustrative purposes only.

Referring now to FIGS. 9-9A, another embodiment hereof is shown in which a ring 907 for coupling a stent-graft prosthesis 900 to a delivery system is woven completely along the inside surface of the graft material of a tubular graft 905. Stent-graft prosthesis 900 is similar to stent-graft prosthesis 200 and includes a tubular graft 905 of graft material which defines a lumen 901. Stent-graft prosthesis 900 is in its fully expanded or deployed configuration but only a first edge 902 of tubular graft 905 is shown in FIG. 9. First or proximal end 902 of stent-graft prosthesis 900 has a closed web configuration in which endmost crowns 908A of a first end stent 906A are covered or lined by tubular graft 905 and do not extend past or beyond first edge 902 of tubular graft 905. First end stent 906A is coupled to an inside surface of tubular graft 905. As described with respect to ring 207, a strand of material is woven around end stent 906A and the ends of the strand are then coupled together to form ring 907 that engages or extends through endmost crowns 908A of first end stent 906A. In this embodiment, however, ring 907 does not pierce or pass through the graft material of tubular graft 905, resulting in a plurality of interior sections or portions 930 that extend between adjacent endmost crowns 908A along an inside surface of tubular graft 905. Besides being woven between endmost crowns 908A of first end stent 906A, ring 907 is not stitched or otherwise attached to prosthesis 900 and is therefore allowed to slide through or freely rotate between the stent crowns. Since interior sections 930 each extend along the inside surface of tubular graft 905, ring 907 restrains or holds open each flap of graft material extending between endmost crowns 908A of first end stent 906A after full deployment, as described above with respect to FIG. 8.

As shown in FIG. 10, alternating sections of ring 907, i.e., every other section 930, may transform into attachment loops 1040 that extend beyond first edge 902 of prosthesis 900 to engage or extend around prongs or fingers of a tip capture mechanism on a delivery system (not shown). In this configuration, the number of attachment loops 1040 that couple to the delivery system is equal to half of the total number of endmost stent crowns. For example, if first end stent 906A includes six endmost stent crowns 908A, three alternating sections 930 of ring 907 form three attachment loops 1040 that engage or extend around fingers of the tip capture mechanism of the delivery system. In another embodiment shown in FIG. 11, all sections 930 of ring 907 may transform into attachment loops 1140 that extend beyond first edge 902 of prosthesis 900 to engage or extend around prongs or fingers of a tip capture mechanism on a delivery system (not shown). In this configuration, the number of attachment loops 1140 that couple to the delivery system is equal to the total number of endmost stent crowns. For example, if first end stent 906A includes six endmost stent crowns 908A, the six sections 930 of ring 907 form six attachment loops 1140 that engage or extend around fingers of the tip capture mechanism of the delivery system. When coupled to a delivery system, first end stent 906A is separated from the tip capture mechanism of the delivery system by attachment loops 1140. Thus, the distance between end stent 906A and the delivery system is equal to the length of attachment loops 1140. The length of each section 930 is approximately equal to the circumference of tubular graft 905 divided by the number of crowns of end stent 906A. When each section 930 forms a loop 1140, the length of each loop 1140 is approximately the length of each section divided by two. For example, if tubular graft 905 has a 40 mm diameter and first end stent 906A has six endmost crowns 908A, the length of each section 930 is approximately equal to (pi*40)/6 or approximately 21 mm and the length of each loop 1140 is approximately equal to 10.5 mm.

The desired number of attachment loops utilized for coupling the prosthesis to the delivery system may depend upon various factors, including but not limited to the number of prongs or fingers of the tip capture mechanism, the desired crossing profile of the delivery system, and the desired diameter of first edge 902 during partial deployment. More particularly, as can be seen from a comparison of the end views of FIG. 10A and FIG. 11A, stent-graft 900 has a smaller end opening when a greater number of attachment loops are utilized for coupling the prosthesis to the delivery system. When alternating sections of ring 907 form three attachment loops 1040 for coupling to the delivery system as shown in FIGS. 10, 10A, the end opening has a diameter $D_1$ which is greater than diameter $D_2$, the diameter of the end opening of FIGS. 11, 11A in which all sections of ring 907 form attachment loops 1140 for coupling to the delivery system. The difference in the end opening diameters is due to the fact that attachment loops 1040 are longer than attachment loops 1140 because the circumference of ring 907 is spread or divided between only three attachment loops 1040 rather than six attachment loops 1140. As can be seen in FIG. 10 and previously described FIG. 7 in which the stent-grafts are in partially deployed configurations, when the attachment loops are longitudinally extended beyond the end of the graft, adjacent crowns of the ring sections that do not form attachment loops are pulled together and the length of attachment loops is increased/maximized. A relatively smaller end opening such as the one shown in FIG. 11A provides the operator with more control if repositioning of the prosthesis is required. However, using alternating sections to the ring to form attachment loops that couple to the delivery system as shown in FIG. 7 and FIG. 10 allow the attachment loops to be longer than if every section of the ring is used, thereby separating the first end stent 906A and the delivery system tip capture mechanism by a greater distance. By increasing the distance between the first end stent 906A and the delivery system tip capture mechanism, a greater length of prosthesis is allowed to deploy or expand into apposition with the vessel wall pre-tip release to prevent the so-called watermelon seed effect as described above.

Figure 12:
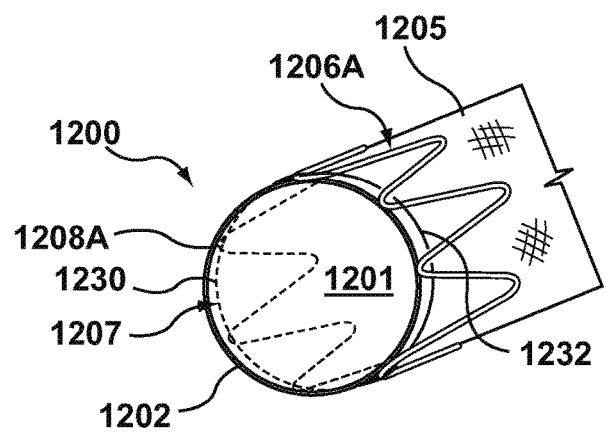
FIG. 12 is a perspective end view of a stent-graft prosthesis having a ring that is woven between adjacent endmost crowns of an end stent of the stent-graft, wherein sections of the ring that extend between adjacent endmost crowns extend along the outside surface of the graft of the stent-graft according to another embodiment hereof.
Figure 12A:
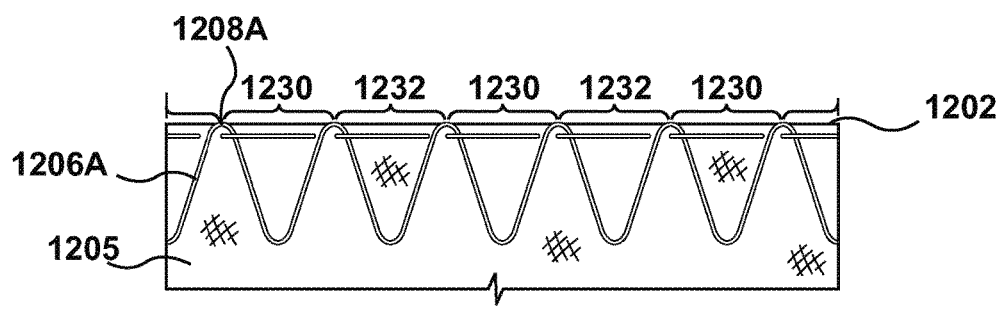
FIG. 12A is a side view of the end of the stent-graft prosthesis of FIG. 12, wherein the stent-graft prosthesis has been cut and laid out flat for illustrative purposes only.

FIGS. 12-12A illustrate another embodiment hereof in which a ring 1207 for coupling a stent-graft prosthesis 1200 to a delivery system is woven completely along the outside surface of the graft material of a tubular graft 1205. Stent-graft prosthesis 1200 is similar to stent-graft prosthesis 200 and includes a tubular graft 1205 of graft material which defines a lumen 1201. Stent-graft prosthesis 1200 is in its fully expanded or deployed configuration but only a first edge 1202 of tubular graft 1205 is shown in FIG. 12. First edge 1202 of stent-graft prosthesis 1200 has a closed web configuration in which endmost crowns 1208A of a first end stent 1206A are covered or lined by tubular graft 1205 and do not extend past or beyond first edge 1202 of tubular graft 1205. First end stent 1206A is coupled to an outside surface of tubular graft 1205. As described with respect to ring 207, a strand of material is woven around end stent 1206A and the ends of the strand are then coupled together to form ring 1207 that engages or extends through endmost crowns 1208A of first end stent 1206A. In this embodiment, however, ring 1207 does not pierce or pass through the graft material of tubular graft 1205, resulting in a plurality of exterior sections or portions 1232 that extend between adjacent endmost crowns 1208A along an outside surface of tubular graft 1205. Besides being woven between endmost crowns 1208A of first end stent 1206A, ring 1207 is not stitched or otherwise attached to prosthesis 1200 and is therefore allowed to slide through or freely rotate between the stent crowns. One or more sections 1232 of ring 1207 are utilized for forming attachment loops (not shown) that extend beyond first edge 1202 of prosthesis 1200 to couple the prosthesis to a delivery system (not shown). For example, as explained above with respect to FIGS. 10-11, alternating sections of ring 1207 or all sections of ring 1207 may transform into attachment loops for coupling to the delivery system.

Regardless of the number of attachment loops utilized for coupling the prosthesis to the delivery system, it is essential in all embodiments hereof that the longitudinally-extending attachment loops used to hold the end stent to the delivery system in a delivery configuration retract or retreat back towards the prosthesis such that the ring returns to or resumes its circular shape that lies against the tubular graft distal of a proximal edge of the prosthesis when the end stent is in a fully deployed configuration. As explained above with respect to FIG. 8, the temporary attachment loops are pulled back towards the prosthesis when the end stent is released from the delivery system and self-expands. Thus, the inherent spring forces of the stent ensure that the attachment loops are pulled back so that the ring retracts completely distal of a proximal edge of the tubular graft and encircles the endmost crowns of the end stent. FIGS. 13-18 relate to various features and/or mechanisms to further ensure complete retraction of the attachment loops to the end stent. The features and/or mechanisms to further ensure complete retraction of the attachment loops may be utilized alone or in any combination. Beginning with an embodiment shown in FIG. 13, one or more sections of the ring may be coupled to the graft material of the graft to assist in retraction of the attachment loops. More particularly, stent-graft prosthesis 1300 is similar to stent-graft prosthesis 200 and includes a tubular graft 1305 of graft material which defines a lumen 1301. Stent-graft prosthesis 1300 is in its fully expanded or deployed configuration but only a first proximal end 1302 of tubular graft 1305 is shown in FIG. 13, which has a closed web configuration in which endmost crowns 1308A of a first end stent 1306A are covered or lined by tubular graft 1305 and do not extend past or beyond first edge 1302 of tubular graft 1305. First end stent 1306A is coupled to an outside surface of tubular graft 1305, but may alternatively be coupled to an inside surface thereof. As described with respect to ring 207, a strand of material is woven around end stent 1306A and the ends of the strand are then coupled together to form ring 1307 that engages or extends through endmost crowns 1308A of first end stent 1306A. Ring 1307 is similar to ring 207 in that it passes through the graft material of tubular graft 1305 within each endmost crown 1308A of first end stent 1306A such that ring 1307 includes alternating interior and exterior sections 1330, 1332, respectively, which extend along inside and outside surfaces of tubular graft 1305, respectively. When coupled to a delivery system (not shown), interior sections 1330 that extend along the inside surface of tubular graft 1305 are utilized to transform into attachment loops (not shown) that extend beyond first edge 1302 of prosthesis 1300. One or more stitches 1344 couple or attach exterior sections 1332 of ring 1307 to the graft material of tubular graft 1305. Securing exterior sections 1332 of ring 1307 to tubular graft 1305 assists in retraction of the attachment loops when the prosthesis is fully deployed, because stitches 1344 function as anchors that assist in pulling the attachment loops back towards tubular graft 1305 after stent-graft prosthesis 1300 is fully deployed. Although stitches 1344 are shown with a ring that has alternating interior and exterior sections, it will be understood by one of ordinary skill in the art that the stitches may be utilized in any embodiment described herein, including those in which the ring does not pierce the graft material but rather extends solely along the inside or outside surface of the graft material.

Another embodiment to further ensure complete retraction of the attachment loops to the end stent is shown in FIG. 14 in which the ring is coupled to the stent adjacent to the first end stent. Stent-graft prosthesis 1400 is similar to stent-graft prosthesis 200 and includes a tubular graft 1405 having a first proximal edge or end 1402, a second distal edge or end 1404, and a body 1403 there between which defines a lumen (not shown) through stent-graft prosthesis 1400. Stent-graft prosthesis 1400 is shown in its fully expanded or deployed configuration. Rather than being coupled to the first end stent as shown in FIG. 2, a ring 1407 is coupled to a second stent 1406C, which is next in order to and distal of first end stent 1406A. Ring 1407 is similar to ring 207 in that it passes through the graft material of tubular graft 1405 within each endmost crown 1408C of second stent 1406C such that ring 1407 includes alternating interior and exterior sections 1430, 1432, respectively, which extend along inside and outside surfaces of tubular graft 1405, respectively. Coupling ring 1407 to stent 1406C rather than first end stent 1406A assists in retraction of the attachment loops when the prosthesis is fully deployed, because the spring or deployment force of both stent 1406C and first stent 1406A pull the attachment loops back towards the interior surface of the tubular graft 1405 after stent-graft prosthesis 1400 is fully deployed. Although ring 1407 is shown with alternating interior and exterior sections, it will be understood by one of ordinary skill in the art that the ring may be coupled to stent 1406C via any configuration described herein, including those in which the ring does not pierce the graft material but rather extends solely along the inside or outside surface of the graft material.

Another embodiment to further ensure complete retraction of the attachment loops is shown in FIG. 15 in which one or more sections of the ring are coupled to the stent adjacent to the first end stent. Stent-graft prosthesis 1500 is similar to stent-graft prosthesis 200 and includes a tubular graft 1505 having a first proximal edge or end 1502, a second distal edge or end 1504, and a body 1503 there between which defines a lumen (not shown) through stent-graft prosthesis 1500. Stent-graft prosthesis 1500 is shown in its fully expanded or deployed configuration. As described with respect to ring 207, a strand of material is woven around of end stent 1506A and the ends of the strand are then coupled together to form ring 1507 that engages or extends through endmost crowns 1508A of first end stent 1506A. Ring 1507 is similar to ring 207 in that it passes through the graft material of tubular graft 1505 within each endmost crown 1508A of first end stent 1506A such that ring 1507 includes alternating interior and exterior sections 1530, 1532, respectively, which extend along inside and outside surfaces of tubular graft 1505, respectively. When coupled to a delivery system (not shown), interior sections 1530 that extend along the inside surface of tubular graft 1505 are utilized to form attachment loops (not shown) that extend beyond first edge 1502 of prosthesis 1500. A suture or stitch 1546 couples or attaches an exterior section 1532 of ring 1507 to a stent 1506C, which is adjacent to and distal of first end stent 1506A. Securing one or more exterior sections 1532 of ring 1507 to stent 1506C assists in refraction of the attachment loops when the prosthesis is fully deployed, because suture 1546 functions as an anchor that assists in pulling the attachment loops back towards tubular graft 1505. Although suture 1546 is shown with a ring that has alternating interior and exterior sections, it will be understood by one of ordinary skill in the art that the suture may be utilized in any embodiment described herein, including those in which the ring does not pierce the graft material but rather extends solely along the inside or outside surface of the graft material.

Figure 16:
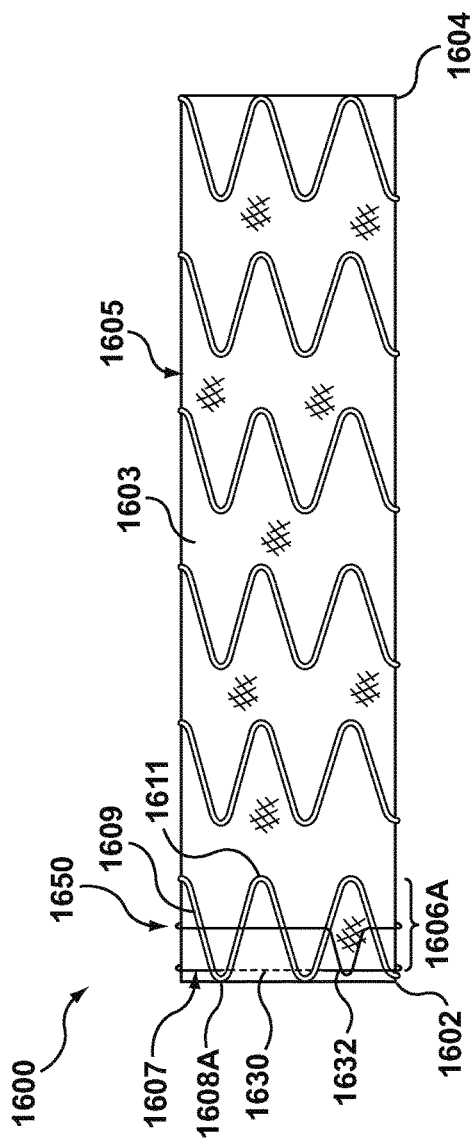
FIG. 16 is a side view of a stent-graft prosthesis having a ring that is woven between adjacent endmost crowns of an end stent of the stent-graft, wherein a second suture ring extends around the struts of the end stent and is intertwined with the ring woven between adjacent endmost crowns of the end stent according to another embodiment hereof.
Figure 17:
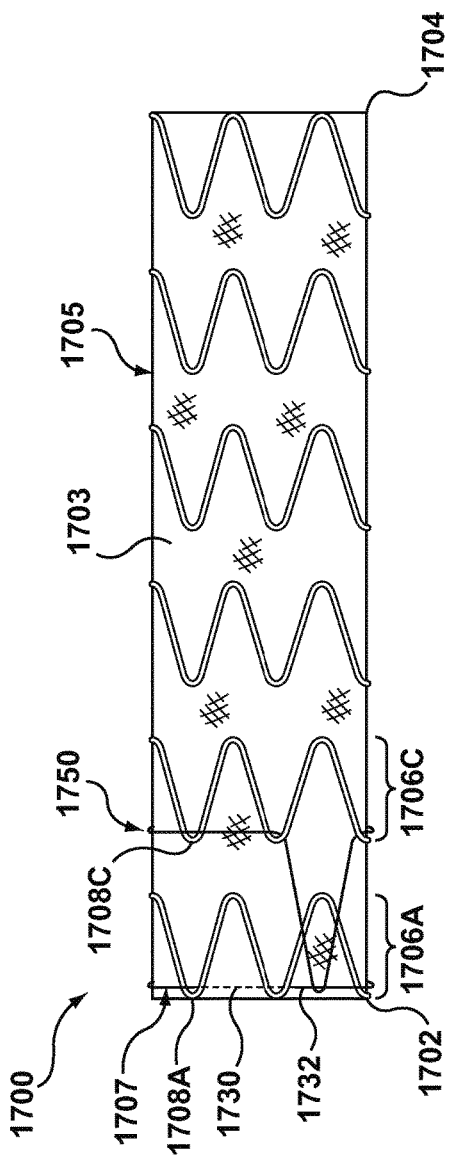
FIG. 17 is a side view of a stent-graft prosthesis having a ring that is woven between adjacent endmost crowns of an end stent of the stent-graft, wherein a second suture ring extends around a stent adjacent to the end stent and is intertwined with the ring woven between adjacent endmost crowns of the end stent according to another embodiment hereof.

Additional embodiments to further ensure complete retraction of the attachment loops are shown in FIG. 16 and FIG. 17, in which a second suture ring functions as an anchor that assists in pulling the attachment loops back towards the graft. In FIG. 16, the second suture ring encircles the first end stent around the struts of the stent, and in FIG. 17, the second suture ring encircles a second stent adjacent to and distal of the first end stent. Referring first to FIG. 16, stent-graft prosthesis 1600 is similar to stent-graft prosthesis 200 and includes a tubular graft 1605 having a first proximal edge or end 1602, a second distal edge or end 1604, and a body 1603 there between which defines a lumen (not shown) through stent-graft prosthesis 1600. Stent-graft prosthesis 1600 is shown in its fully expanded or deployed configuration. As described with respect to ring 207, a strand of material is woven around end stent 1606A and the ends of the strand are then coupled together to form ring 1607 that engages or extends through endmost crowns 1608A of first end stent 1606A. Ring 1607 is similar to ring 207 in that it passes through the graft material of tubular graft 1605 within each endmost crown 1608A of first end stent 1606A such that ring 1607 includes alternating interior and exterior sections 1630, 1632, respectively, which extend along inside and outside surfaces of tubular graft 1605, respectively. When coupled to a delivery system (not shown), interior sections 1630 that extend along the inside surface of tubular graft 1605 are utilized to form attachment loops (not shown) that extend beyond first edge 1602 of prosthesis 1600. Ring 1607 has a diameter substantially equal to the expanded diameter of first end stent 1606A. A second suture ring 1650 is coupled to and encircles first end stent 1606A, around struts 1609 of first end stent 1606A. Second suture ring 1650 may be woven between adjacent struts 1609 and/or coupled to struts 1609 via stitching. In an alternative embodiment (not shown), second suture ring 1650 may encircle first end stent 1606A around a second or opposing set of crowns 1611. Second suture ring 1650 hooks or loops around ring 1607 at least one intersection point on at least one exterior section 1632 so that it may act as an anchor that assists in pulling the attachment loops back towards the interior surface of the tubular graft 1605. Although second suture ring 1650 is shown as looping around only one exterior section 1632 in FIG. 16, it will be understood by one of ordinary skill in the art that second suture ring 1650 may loop around any section of ring 1607 that is not utilized to form attachment loops that extend beyond the first edge of the prosthesis during delivery. The length of second suture ring 1650 is longer than the length of the strand utilized for form ring 1607 because second suture ring 1650 is extends around the circumference of stent-graft prosthesis 1600 and also extends longitudinally to interface with ring 1607. The length of second suture ring 1650 varies depending upon how many sections of ring 1607 it loops around. In another embodiment (not shown), ring 1607 may have a diameter greater than the expanded diameter of first end stent 1606A to facilitate the interface or intersection with second suture ring 1650. Although attachment ring 1607 is shown with alternating interior and exterior sections, it will be understood by one of ordinary skill in the art that second suture ring 1650 may be utilized in any embodiment described herein, including those in which the attachment ring does not pierce the graft material but rather extends solely along the inside or outside surface of the graft material.

The embodiment of FIG. 17 is similar to that of FIG. 16 except that the second suture ring is coupled to a second stent adjacent to and distal of the first end stent. More particularly, stent-graft prosthesis 1700 includes a tubular graft 1705 having a first proximal edge or end 1702, a second distal edge or end 1704, and a body 1703 there between which defines a lumen (not shown) through stent-graft prosthesis 1700. Stent-graft prosthesis 1700 is shown in its fully expanded or deployed configuration. As described with respect to ring 207, a strand of material is woven around end stent 1706A and the ends of the strand are then coupled together to form ring 1707 that engages or extends through endmost crowns 1708A of first end stent 1706A. Ring 1707 is similar to ring 207 in that it passes through the graft material of tubular graft 1705 within each endmost crown 1708A of first end stent 1706A such that ring 1707 includes alternating interior and exterior sections 1730, 1732, respectively, which extend along inside and outside surfaces of tubular graft 1705, respectively. When coupled to a delivery system (not shown), interior sections 1730 that extend along the inside surface of tubular graft 1705 are utilized to form attachment loops (not shown) that extend beyond first edge 1702 of prosthesis 1700. Ring 1707 has a diameter substantially equal to the expanded diameter of first end stent 1706A. A second suture ring 1750 is woven between endmost crowns 1708C of a stent 1706C, which is next in order to and distal of first end stent 1606A. Second suture ring 1750 may be woven between adjacent endmost crowns 1708C and/or coupled to stent 1706C via stitching. Second suture ring 1750 wraps or loops around ring 1707 at least one intersection point on at least one exterior section 1732 so that it may act as an anchor that assists in pulling the loops back towards the interior surface of the tubular graft 1705. Although second suture ring 1750 is shown as looping around only one exterior section 1732 in FIG. 17, it will be understood by one of ordinary skill in the art that second suture ring 1750 may loop around any section of ring 1707 that is not utilized to form attachment loops that extend beyond the first edge of the prosthesis during delivery. The length of second suture ring 1750 is longer than the length of the strand utilized for form ring 1707 because second suture ring 1750 is extends around the circumference of stent-graft prosthesis 1700 and also extends longitudinally to interface with ring 1707. The length of second suture ring 1750 varies depending upon how many sections of ring 1707 it loops around. In another embodiment (not shown), ring 1707 may have a diameter greater than the expanded diameter of first end stent 1706A to facilitate the interface or intersection with second suture ring 1750. Although attachment ring 1707 is shown with alternating interior and exterior sections, it will be understood by one of ordinary skill in the art that second suture ring 1750 may be utilized in any embodiment described herein, including those in which the attachment ring does not pierce the graft material but rather extends solely along the inside or outside surface of the graft material.

Figure 18:
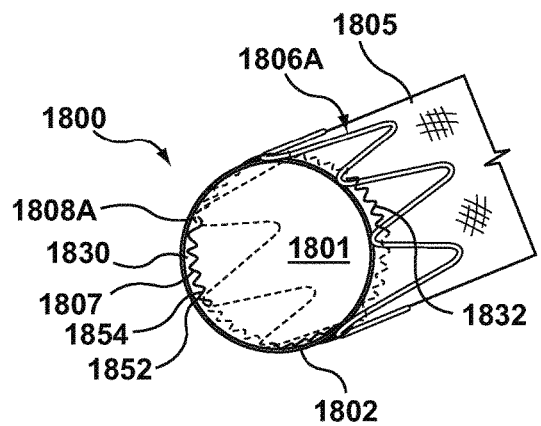
FIG. 18 is a perspective end view of a stent-graft prosthesis having a ring that is woven between adjacent endmost crowns of an end stent of the stent-graft, wherein the ring has a sinusoidal shape-set configuration according to an embodiment hereof.

Another embodiment to further ensure complete retraction of the attachment loops is shown in FIG. 18 in which the ring has a sinusoidal shape-set configuration. Stent-graft prosthesis 1800 is similar to stent-graft prosthesis 200 and includes a tubular graft 1805 of graft material which defines a lumen 1801. Stent-graft prosthesis 1800 is in its fully expanded or deployed configuration but only a first proximal end 1802 of tubular graft 1805 is shown in FIG. 18. First edge 1802 of stent-graft prosthesis 1800 has a closed web configuration in which endmost crowns 1808A of a first end stent 1806A are covered or lined by tubular graft 1805 and do not extend past or beyond first edge 1802 of tubular graft 1805. Ring 1807 is similar to ring 207 in that it passes through the graft material of tubular graft 1805 within each endmost crown 1808A of first end stent 1806A such that ring 1807 includes alternating interior and exterior sections 1830, 1832, respectively, which extend along inside and outside surfaces of tubular graft 1805, respectively. When coupled to a delivery system (not shown), interior sections 1830 that extend along the inside surface of tubular graft 1805 are utilized to form attachment loops (not shown) that extend beyond first edge 1802 of prosthesis 1800. In order to assist in retraction of the attachment loops when the prosthesis is fully deployed, ring 1807 is constructed from a self-expanding or spring material, such as Nitinol, and is a shape-set sinusoidal patterned ring including a plurality of crowns or bends 1852 and a plurality of struts or straight segments 1854 with each crown being formed between a pair of opposing struts. In an embodiment, the length of struts 1854 of ring 1807 ranges from the same as the length of the struts on first end stent 1806A to 1/10 of the length of the struts on first end stent 1806A. In an embodiment, the number of sinusoids of ring 1807 ranges from 1/3 the number of sinusoids of first end stent 1806A to twenty times the number of sinusoids of first end stent 1806A. Ring 1807 is thus from a material that can be provided with a mechanical memory to return or recoil the ring from a delivery configuration in which interior sections 1830 transform attachment loops that extend beyond first edge 1802 of prosthesis 1800 to an expanded deployed configuration in which the attachment loops retract completely into tubular graft 1805. Although ring 1807 is shown with alternating interior and exterior sections, it will be understood by one of ordinary skill in the art that the ring may be coupled to first end stent 1806A via any configuration described herein, including those in which the ring does not pierce the graft material but rather extends solely along the inside or outside surface of the graft material.

Figure 19:
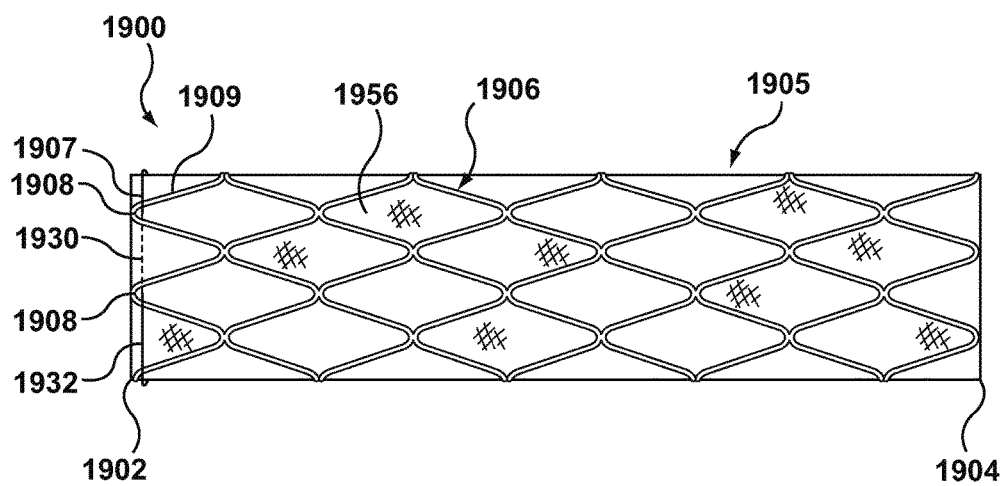
FIG. 19 is a side view of a stent-graft having a stent configuration according to another embodiment hereof, wherein a ring is woven between adjacent endmost crowns of an end stent of the stent-graft according to an embodiment hereof.

In the above embodiments, the scaffolding or support of the stent-graft prostheses have been illustrated as a series of independent or separate self-expanding stents/sinusoidal patterned rings. However, as will be understood by one of ordinary skill in the art, the support structure or scaffolding of a stent-graft prosthesis may have other configurations such as a series of sinusoidal patterned rings coupled to each other to form a self-expanding stent. In another embodiment, the support structure or scaffolding of a stent-graft prosthesis may be a unitary tubular component such as but not limited to the configuration shown in FIG. 19. FIG. 19 illustrates a stent-graft prosthesis 1900 according to another embodiment hereof in which the prosthesis includes a tubular radially-compressible stent or scaffold 1906 rather than a plurality of stents formed as independent sinusoidal patterned rings. Stent-graft prosthesis 1900 is shown in its fully expanded or deployed configuration. Stent 1906 is coupled to a tubular graft 1905 to extend from a first proximal end 1902 to a second distal end 1904 thereof for supporting the graft material and is operable to self-expand into apposition with an interior wall of a body vessel (not shown). In the embodiment depicted in FIG. 19, stent 1906 is a unitary tubular component having diamond-shaped openings 1956, which may be formed by various conventional stent forming methods as would be understood by one of ordinary skill in the art. Stent 1906 includes endmost crowns 1908 that are proximate to and inwardly spaced from first edge 1902 of tubular graft 1905. Each endmost crown 1908 is a curved segment extending between opposing struts 1909 on stent 1906. Ring 1907 is similar to ring 207 in that it passes through the graft material of tubular graft 1905 within each endmost crown 1908A of first end stent 1906A such that ring 1907 includes alternating interior and exterior sections 1930, 1932, respectively, which extend along inside and outside surfaces of tubular graft 1905, respectively. When coupled to a delivery system (not shown), interior sections 1930 that extend along the inside surface of tubular graft 1905 are utilized to form attachment loops (not shown) that extend beyond first edge 1902 of prosthesis 1900. Although attachment ring 1907 is shown with alternating interior and exterior sections, it will be understood by one of ordinary skill in the art that the ring may be coupled to stent 1906 via any configuration described herein, including those in which the ring does not pierce the graft material but rather extends solely along the inside or outside surface of the graft material.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A prosthesis for implantation within a body lumen, the prosthesis being configured for delivery via a catheter having a tip capture mechanism at a distal end thereof, the tip capture mechanism including at least a first tip capture finger and a second tip capture finger, the prosthesis comprising:
   a tubular graft of a graft material;
   a stent coupled to the tubular graft and including a plurality of crowns and a plurality of struts with each crown being formed between a pair of opposing struts, the stent having endmost crowns that are adjacent to and distal of a proximal edge of the tubular graft, wherein the endmost crowns are secured to the graft material of the tubular graft; and
   a ring that directly engages the endmost crowns of the stent, wherein the ring includes a plurality of integral sections that collectively form the ring and each integral section extends between two endmost crowns when the stent is in a compressed delivery configuration, and wherein each of a first integral section of the ring and a second integral section of the ring longitudinally extends beyond the proximal edge of the tubular graft as an attachment loop of the prosthesis that is configured to engage the first tip capture finger and the second tip capture finger, respectively, of the catheter when the stent is in the compressed delivery configuration, the first and second integral sections being disposed at opposing locations of the stent, and wherein each of the first integral section of the ring and the second integral section of the ring do not longitudinally extend beyond the proximal edge of the tubular graft when the stent is in an expanded deployed configuration.

2. The prosthesis of claim 1, wherein the ring is a circular band when the stent is in the expanded deployed configuration.

3. The prosthesis of claim 1, wherein the ring has a sinusoidal shape-set configuration when the stent is in the expanded deployed configuration.

4. The prosthesis of claim 1, wherein each integral section of the ring extends between a pair of adjacent endmost crowns.

5. The prosthesis of claim 1, wherein the ring pierces the graft material of the tubular graft and the plurality of integral sections of the ring alternate between inside and outside surfaces of the tubular graft.

6. The prosthesis of claim 1, wherein the stent is coupled to an inside surface of the tubular graft and wherein the ring directly engages the endmost crowns without piercing the graft material of the tubular graft.

7. The prosthesis of claim 1, wherein the stent is coupled to an outside surface of the tubular graft and wherein the ring directly engages the endmost crowns without piercing the graft material of the tubular graft.

8. The prosthesis of claim 1, wherein all of the plurality of integral sections of the ring form attachment loops that longitudinally extend beyond the proximal edge of the tubular graft when the stent is in the compressed delivery configuration.

9. The prosthesis of claim 1, wherein every other integral section of the ring forms attachment loops that longitudinally extend beyond the proximal edge of the tubular graft when the stent is in the compressed delivery configuration.

10. The prosthesis of claim 9, wherein the integral sections of the ring that do not form attachment loops are coupled to the graft material of the tubular graft.

11. The prosthesis of claim 1, further comprising: a plurality of stents coupled to a body of the tubular graft, wherein each stent is a sinusoidal patterned ring having a first set of crowns near the proximal edge of the tubular graft and a second set of crowns distant from the proximal edge of the tubular graft relative to the first set of crowns.

12. The prosthesis of claim 11, wherein the ring directly engages endmost crowns of a first stent most proximate to the proximal edge of the tubular graft.

13. The prosthesis of claim 12, further comprising: at least one suture extending between a second stent adjacent to the first stent and an integral section of the ring that does not form an attachment loop.

14. The prosthesis of claim 12, further comprising: a second ring coupled to struts of the first stent, wherein the second ring loops around the ring at at least one intersection point on an integral section of the ring that does not form an attachment loop that longitudinally extends beyond the proximal edge of the tubular graft.

15. The prosthesis of claim 12, further comprising: a second ring coupled to a second stent adjacent to the first stent, wherein the second ring loops around the ring at at least one intersection point on an integral section of the ring that does not form an attachment loop that longitudinally extends beyond the proximal edge of the tubular graft.

16. The prosthesis of claim 11, wherein the ring directly engages the first set of crowns of a second stent adjacent to a first stent most proximate to the proximal edge of the tubular graft.

17. The prosthesis of claim 1, wherein the stent is coupled to the tubular graft to extend from the proximal edge of the tubular graft to a distal edge of the tubular graft.

18. The prosthesis of claim 1, wherein the ring directly engages the endmost crowns of the stent by being woven between adjacent endmost crowns of the stent.

19. A delivery system for implanting a stent-graft prosthesis within a body lumen, the delivery system comprising:
- a catheter including an outer delivery sheath and a catheter shaft slidingly disposed within the outer delivery sheath, the catheter shaft having a tip capture mechanism at a distal end thereof, wherein the tip capture mechanism includes a first tip capture finger and a second tip capture finger; and
- a stent-graft prosthesis mounted on the catheter shaft proximal to the tip capture mechanism at the distal end of the catheter shaft, the stent-graft prosthesis including a stent coupled to a tubular graft of a graft material, wherein the stent includes a plurality of crowns and a plurality of struts with each crown being formed between a pair of opposing struts, and endmost crowns that are adjacent to and distal of a proximal edge of the tubular graft and secured to the graft material of the tubular graft;
- wherein a ring directly engages the endmost crowns of the stent, a section of the ring being defined as the portion which extends between two endmost crowns when the stent is in a compressed delivery configuration, and wherein each of a first section of the ring and a second section of the ring longitudinally extends beyond the proximal edge of the tubular graft as an attachment loop of the stent-graft prosthesis that engages the first tip capture finger and the second tip capture finger, respectively, when the stent is in the compressed delivery configuration, the first and second integral sections being disposed at opposing locations of the stent, and wherein each of the first section of the ring and the second section of the ring do not longitudinally extend beyond the proximal edge of the tubular graft when the stent is in an expanded deployed configuration.

20. A prosthesis for implantation within a body lumen, the prosthesis being configured for delivery via a catheter having a tip capture mechanism at a distal end thereof, the tip capture mechanism including a first tip capture finger and a second tip capture finger, the prosthesis comprising:
- a tubular graft of a graft material;
- a stent coupled to the tubular graft and including a plurality of crowns and a plurality of struts with each crown being formed between a pair of opposing struts, the stent having endmost crowns that are adjacent to and distal of a proximal edge of the tubular graft, wherein the endmost crowns are secured to the graft material of the tubular graft; and
- a ring that directly engages the endmost crowns of the stent, a section of the ring being defined as the portion which extends between two endmost crowns when the stent is in a compressed delivery configuration, wherein each of a first section of the ring and a second section of the ring transforms into an attachment loop of the prosthesis that longitudinally extends beyond the proximal edge of the tubular graft and is configured to engage the first tip capture finger and the second tip capture finger, respectively, of the catheter when the stent is in the compressed delivery configuration, the first and second integral sections being disposed at opposing locations of the stent, and wherein each of the first section of the ring and the second section of the ring retracts into the stent when the stent is in an expanded deployed configuration so that the ring has a diameter that is substantially equal to an expanded diameter of the stent.

* * * * *